United States Patent [19]

Pena

[11] Patent Number: 5,178,133

[45] Date of Patent: Jan. 12, 1993

[54] LAPAROSCOPIC RETRACTOR AND SHEATH

[76] Inventor: Louis T. Pena, 15523 Barbarossa Dr., Houston, Tex. 77083

[21] Appl. No.: 674,892

[22] Filed: Mar. 26, 1991

[51] Int. Cl.⁵ .............................................. A61B 17/02
[52] U.S. Cl. ................................... 128/20; 604/105; 604/108; 606/198
[58] Field of Search ............... 128/20, 844; 604/105, 604/106, 107, 108, 109; 24/569

[56] References Cited

U.S. PATENT DOCUMENTS

| | | | |
|---|---|---|---|
| 1,392,085 | 9/1921 | Stanton | 604/108 |
| 1,412,975 | 4/1922 | Stanton | 604/108 |
| 1,434,964 | 11/1922 | Rosa | 604/108 |
| 1,585,815 | 5/1926 | Andrews et al. | 604/108 |
| 2,617,914 | 11/1952 | Keller et al. | 24/569 |
| 2,642,767 | 6/1953 | Kesher | 24/569 |
| 3,495,586 | 2/1970 | Reganbogen | 606/198 |
| 4,043,338 | 8/1977 | Homm et al. | 604/105 |
| 4,585,000 | 4/1986 | Hershenson | 604/108 |
| 4,648,402 | 3/1987 | Santos | 606/198 |
| 4,660,571 | 4/1987 | Hess et al. | 604/105 |
| 4,792,600 | 1/1989 | Meadows | 128/844 |
| 4,881,553 | 11/1989 | Grossman | 128/844 |
| 5,041,093 | 8/1991 | Chu | 606/198 |
| 5,074,314 | 12/1991 | Wilson | 128/844 |

Primary Examiner—Paul J. Hirsch

[57] ABSTRACT

A laparoscopic retractor is shown for manually maneuvering tissue which would otherwise obstruct the view from the operative site. Laparoscopy is a method of visually examining the peritoneal cavity by means of a long slender endoscope (laparoscope) equipped with sheath, obturator, biiopsy forceps, a sphygmo-manometer bulb and tubing, and a syringe. The laparoscope is introduced into the peritoneal cavity by a small incision in the abdominal wall. Laparoscopic surgery is surgery done through the tube of a laparoscope. The retractor is an instrument which is sized for insertion through the laparoscope tube and comprises a pair of arms, which are opened with a scissors motion, and a supporting handle. The arms preferably have a membrane or sheath supported between them which is spread apart by opening the arms. In a preferred embodiment, the arms are covered by a tubular latex sheath, similar to a condom, which is spread apart on opening movement of the arms of the instrument. The instrument is inserted, with the arms closed, through the laparoscopic tube into the peritoneal cavity. After the tissue or organ has been located by viewing the laparoscope, the arms of the instrument are opened by operation of the handle to spread the covering membrane. The opened arms, with membrane stretched therebetween, is then moved to displace the tissue or organ to allow the surgeon optimal viewing of the surgical field.

9 Claims, 5 Drawing Sheets

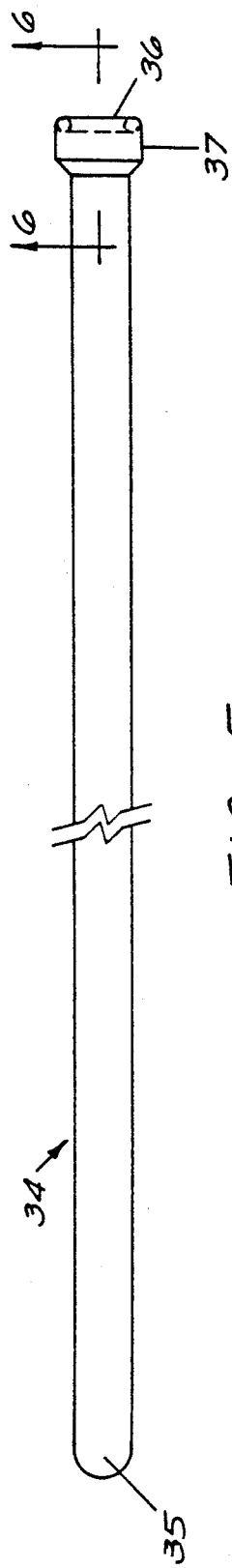
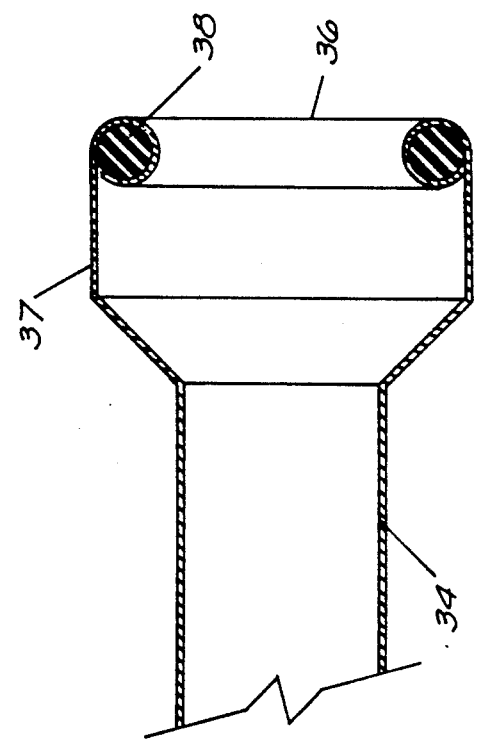
FIG. 5
FIG. 6

LAPAROSCOPIC RETRACTOR AND SHEATH

BACKGROUND OF THE INVENTION

1. FIELD OF THE INVENTION

This invention relates generally to surgical instruments, especially surgical retractors, and more particularly to retractors for use in laparoscopy.

2. BRIEF DESCRIPTION OF THE PRIOR ART

Laparoscopy is a well known method of visually examining the peritoneal cavity by means of a long slender endoscope (laparoscope) equipped with sheath, obturator, biopsy forceps, a sphygmo-manometer bulb and tubing, and a syringe. The laparoscope is introduced into the peritoneal cavity by a small incision in the abdominal wall. Laparoscopic surgery is surgery done through the tube of a laparoscope. Surgical retractors are commonly used for a variety of types of surgery but none are available which can be inserted through a laparoscopic tube for use in laparoscopic viewing and surgery.

There are several patents which disclose instruments used in laparoscopy and retractors for use in other types of surgery.

Kadavy U.S. Pat. No. 1,947,649 discloses an instrument which retains the abdominal viscera away from the wound in suturing the peritoneum.

Sherwin U.S. Pat. No. 3,750,652 discloses a surgical retractor used in knee surgery.

Williams U.S. Pat. No. 4,034,746 discloses a forceps or surgical retractor for use in microsurgery but is not capable of use by insertion through a laparoscopic tube.

Burgin U.S Pat. No. 4,502,485 discloses a disposable plastic forceps or dilator for dilating a surgical incision.

Greenberg U.S. Pat. No. 4,573,452 discloses a surgical holder for laparoscopes and the like. The holder supports the laparoscope mechanically the free the hands of the surgeon.

The present invention is distinguished over the prior art in general, and these patents in particular by providing a laparoscopic retractor for manually maneuvering tissue which would otherwise obstruct the view from the operative site. The retractor is an instrument which is sized for insertion through the laparoscope tube and comprises a pair of arms, which are opened with a scissors motion, and a supporting handle. The arms preferably have a membrane or sheath supported between them which is spread apart by opening the arms. In a preferred embodiment, the arms are covered by a tubular latex sheath, similar to a condom, which is spread apart on opening movement of the arms of the instrument. The instrument is inserted, with the arms closed, through the laparoscopic tube into the peritoneal cavity. After the tissue or organ has been located by viewing the laparoscope, the arms of the instrument are opened by operation of the handle to spread the covering membrane The opened arms and stretched membrane are opened inside the peritoneal cavity then moved to displace the tissue or organ to allow the surgeon optimal viewing of the surgical field.

SUMMARY OF THE INVENTION

It is therefore an object of the present invention to provide a new and improved retractor for use in laparoscopy and laparoscopic surgery.

It is another object of this invention to provide a new and improved retractor for use in laparoscopy and laparoscopic surgery which can be inserted through a small incision and opened inside the peritoneal cavity.

It is another object of this invention to provide a new and improved retractor for use in laparoscopy and laparoscopic surgery which can be inserted through a small incision and opened inside the peritoneal cavity and then moved to displace the tissue or organ to allow the surgeon optimal viewing of the surgical field.

Another object of this invention is to provide a new and improved retractor for use in laparoscopy and laparoscopic surgery which can be inserted through the laparoscopic tube.

Another object of this invention is to provide a new and improved retractor for use in laparoscopy and laparoscopic surgery which can be inserted through the laparoscopic tube and then moved to displace the tissue or organ to allow the surgeon optimal viewing of the surgical field.

Another object of this invention is to provide a new and improved retractor for use in laparoscopy and laparoscopic surgery which can be inserted through the laparoscopic tube and opened inside the peritoneal cavity.

Another object of this invention is to provide a new and improved retractor for use in laparoscopy and laparoscopic surgery which can be inserted through the laparoscopic tube and opened inside the peritoneal cavity which includes a membranes or sheath which is spread out and then moved to displace the tissue or organ to allow the surgeon optimal viewing of the surgical field.

Still another object of this invention is to provide a new and improved retractor for use in laparoscopy and laparoscopic surgery which can be inserted through the laparoscopic tube and opened inside the peritoneal cavity which includes a surrounding latex sheath which is spread out and then moved to displace the tissue or organ to allow the surgeon optimal viewing of the surgical field.

Other objects of the invention will become apparent from time to time throughout the specification and claims as hereinafter related.

The above noted objects and other objects of the invention are accomplished by a novel laparoscopic retractor.for manually maneuvering tissue which would otherwise obstruct the view from the operative site. The retractor is an instrument which is sized for insertion through the laparoscope tube and comprises a pair of arms, which are opened with a scissors motion, and a supporting handle. The arms preferably have a membrane or sheath supported between them which is spread apart by opening the arms. In a preferred embodiment, the arms are covered by a tubular latex sheath, similar to a condom, which is spread apart on opening movement of the arms of the instrument. The instrument is inserted, with the arms closed, through the laparoscopic tube into the peritoneal cavity. After the tissue or organ has been located by viewing the laparoscope, the arms of the instrument are opened by operation of the handle to spread the covering membrane. The opened arms and stretched membrane are opened inside the peritoneal cavity then moved to displace the tissue or organ to allow the surgeon optimal viewing of the surgical field.

BRIEF DESCRIPTION OF THE DRAWINGS

FIG. 3A is a section on the line 3A—3A of FIG. 3 showing the configuration of the passage for the actuating rod.

FIG. 5 is a detail elevation of a latex sheath used in the laparoscopic retractor, as shown in FIG. 1.

FIG. 6 is a detail section of the end of a latex sheath used in the laparoscopic retractor, as shown in FIG. 5.

DESCRIPTION OF THE PREFERRED EMBODIMENT

Figure 1:
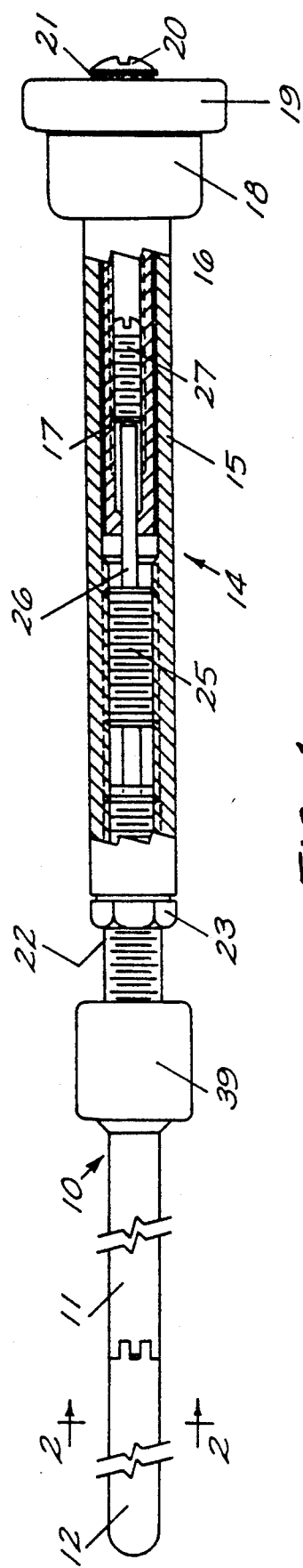
FIG. 1 is a front elevation, with the handle portion in center section, of a laparoscopic retractor with the operating arms in a closed position, illustrating a preferred embodiment of this invention.

Referring to the drawings by numerals of reference there is shown a laparoscopic retractor 10 comprising a center support tube 11 with two operating arms 12 and a reciprocally movable actuating rod 13 at one end and a handle assembly 14 at the other end. The components of retractor 10 are of surgical stainless steel and sized (maximum diameter approximately 14.5-15.0 mm. diameter and 500 mm. length) to fit through a laparoscopic tube along with the laparoscope.

The handle assembly 14 comprises a tubular actuator housing 15 internally threaded at one end and having an enlarged threaded end portion 16. An actuator shaft 17 fits rotatably in the housing 15. An internal shaft retention cap nut 18 is pressed over the end of actuator shaft 17 and is threadedly connected on housing end portion 16. An operating knob 19 is pressed on the end of actuator shaft 17 and secured by trusshead screw 20 and lock washer 21. Rotary movement of knob 19 on threaded housing end portion 16 rotates actuator shaft 17 and moves the shaft rotatably forward and backward.

Figure 4:
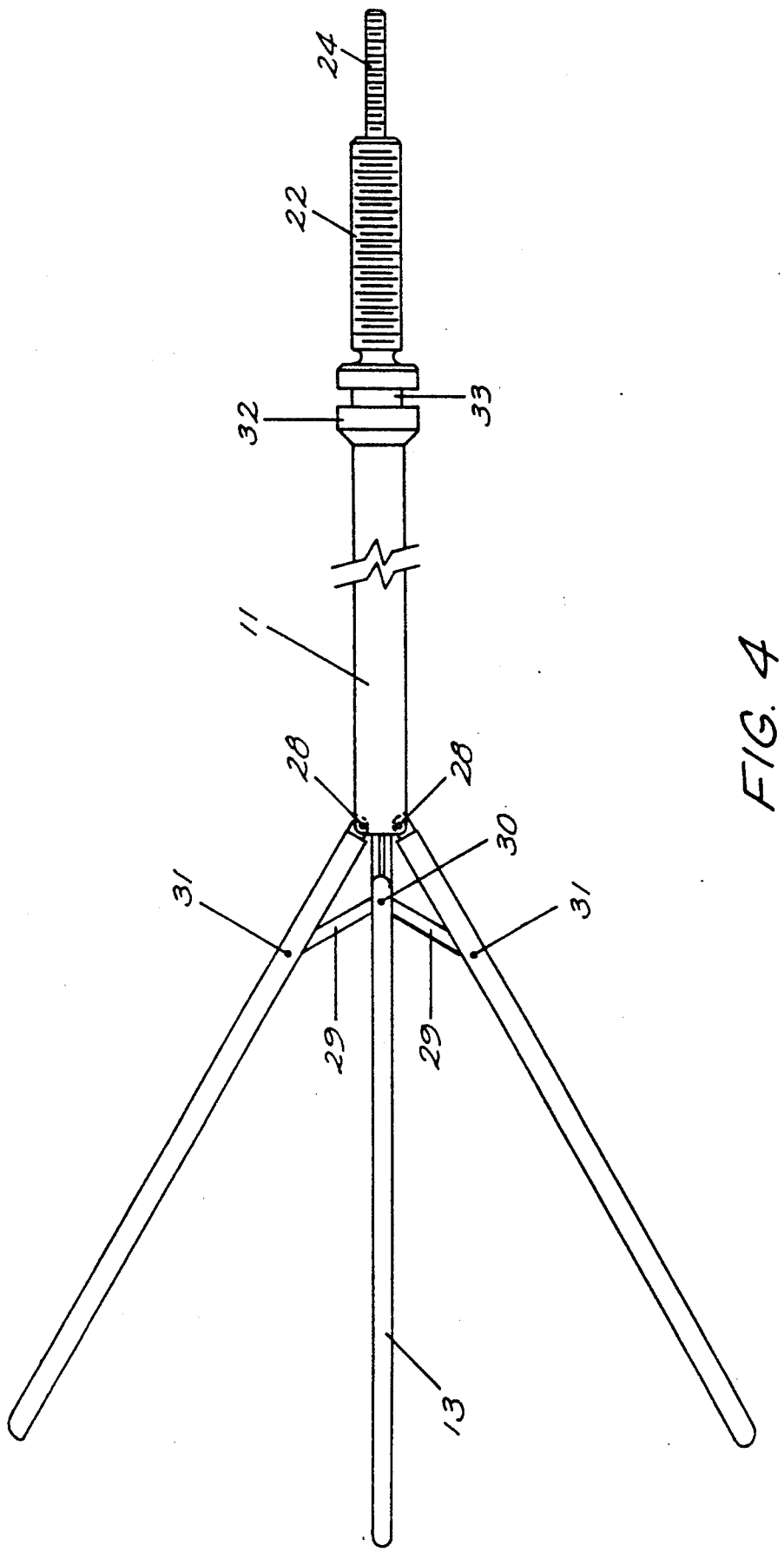
FIG. 4 is a front elevation, with the handle portion removed, of a laparoscopic retractor, as shown in FIG. 1, with the operating arms in an open position
Figure 7:
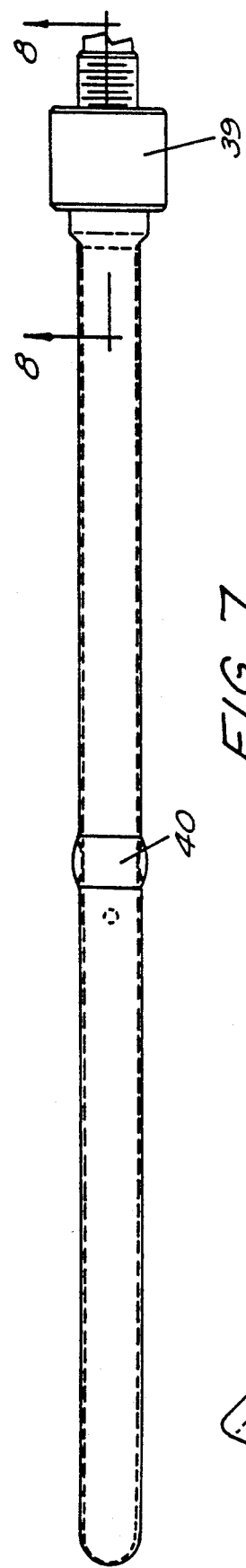
FIG. 7 is a front elevation, with the handle portion removed, of a laparoscopic retractor, as shown in FIG. 1, with the operating arms in a closed position.
Figure 8:
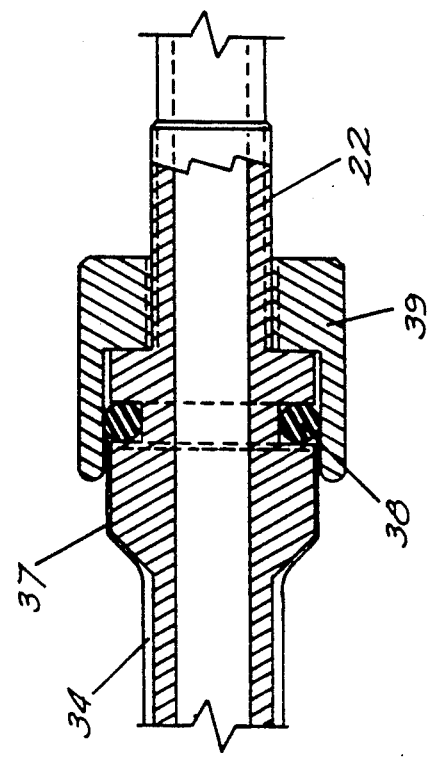
FIG. 8 is a detail section showing the connection of the sheath of FIGS. 5 and 6 to the laparoscopic retractor.

Center support tube 11 has a threaded end portion 22 threadedly secured in the internally threaded end of housing 15. A jam nut 23 secures housing 15 against further movement on center support tube threaded end portion 22. Reciprocally movable actuating rod 13 extends through support tube 11 and has a threaded end portion 24 (FIG. 4).

A threaded actuator screw 25 is threaded in the internally threaded end of housing 15 and has a square tang 26 extending through a square hole in the end of actuator shaft 17 for rotary movement thereby. A set screw 27 is threaded inside actuator shaft 17 to abut the end of square tang 26. Rotary movement of knob 19 on threaded housing end portion 16 therefore rotates actuator shaft 17 and threaded actuator screw 25 together. Threaded actuator screw 25 is internally threaded at the end opposite tang 26 and the threaded end portion 24 of actuator rod 13 is threaded therein for movement by knob 19, actuator shaft 17 and actuator screw 25.

Figure 3:
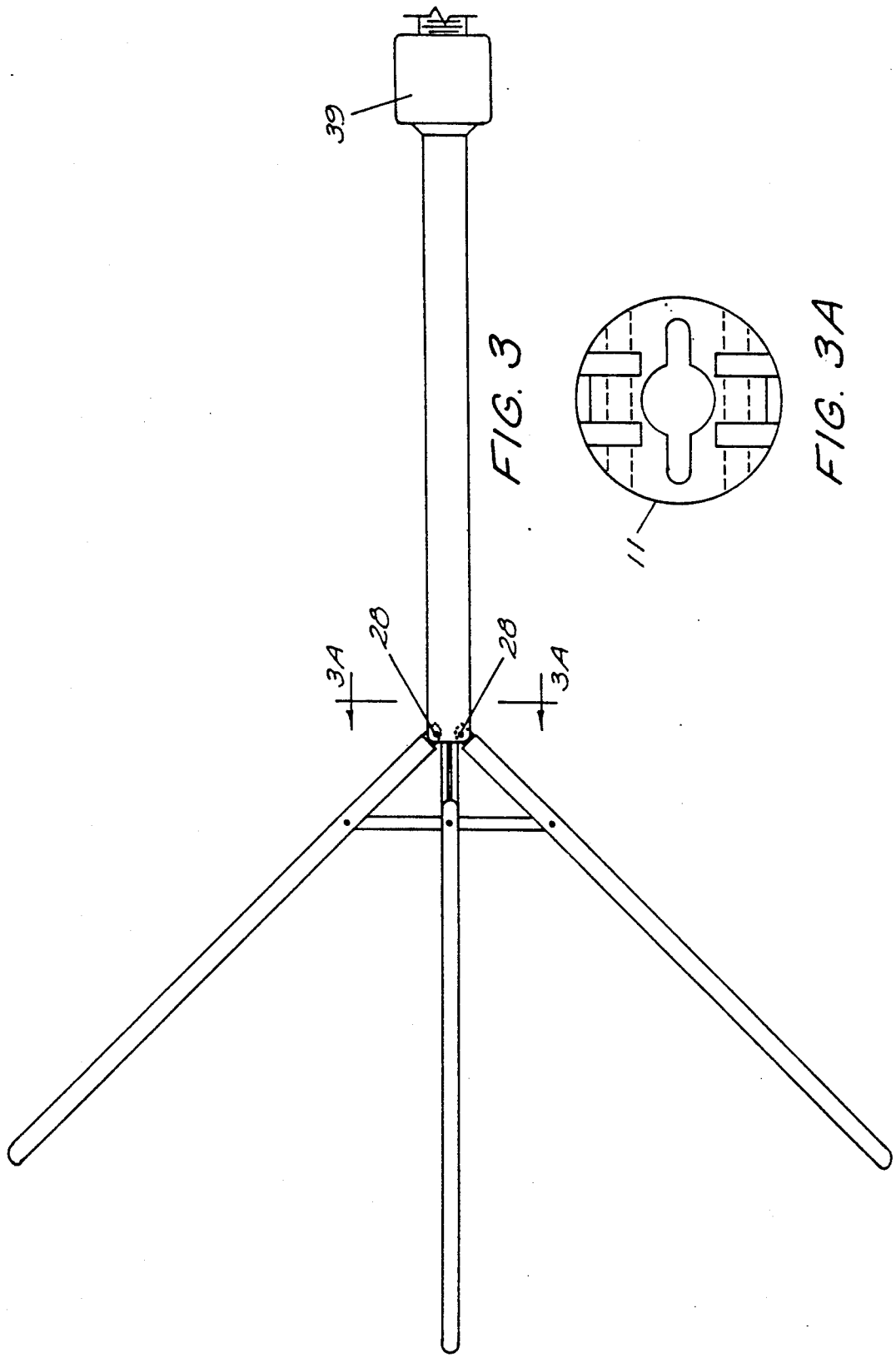
FIG. 3 is a front elevation, with the handle portion in center section, of a laparoscopic retractor, as shown in FIG. 1, with the operating arms in an open position.

Operating arms 12 at said one end of support tube 11 are pivotally supported thereon by pivot pins 28 (FIGS. 3 & 4) and are pivotable outward from their closed position enclosing actuator rod 13. Links 29 are pivotally connected by pins 30 to actuator rod 13 and by pins 31 to operating arms 12. The end of actuator rod 13 enclosed by operating arms 12 is of substantially rectangular cross section and is positioned in a recess of like cross section (FIG. 3A) in support tube 11 which restrains actuator rod 13 from rotation.

Figure 2:
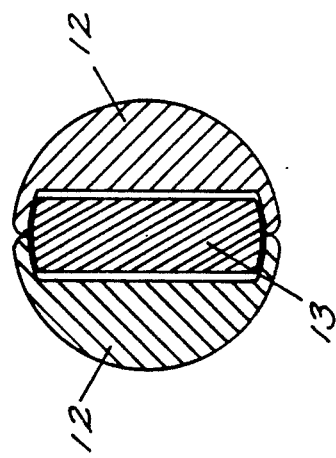
FIG. 2 is a section on the line 2—2 of FIG. 1 showing the relation of the operating arms to the actuating rod.

Rotary movement of knob 19 on threaded housing end portion 16 therefore rotates actuator shaft 17 and threaded actuator screw 25 on threaded end portion 24 of actuator rod 13 and, since rod 13 is restrained from rotation, it is moved forward and backward in support tube 11. Forward and backward movement of rod 13 operates links 29 to pivot arms 12 outward and inward between the closed position shown in FIGS. 1&2 and the opened position. The maximum opened position is that shown in FIG. 3.

Support tube 11 has an enlarged portion 32 and peripheral groove 33 (FIGS. 4, 7 & 8) adjacent to threaded end portion 22 for retaining a latex sheath as described below. The retractor 10 is used in connection with a latex sheath 34. "Latex" as used herein means a surgical or medical tubular rubber membrane similar to a condom or equivalent elastic membrane material. Latex sheath 34, shown in FIGS. 5-9, is a rubber tube about 9 mm. diameter and 315 mm. long having a closed end 35 and open end 36. Sheath 34 has a substantially enlarged (14.5 mm.) portion 37 adjacent to open end 36 which is bonded to a rubber 0-ring 38 which functions to secure the sheath over operating arms 12 during use.

Sheath 34 is installed on the two operating arms 12 with end portion 37 fitted over support tube enlarged portion 32 and 0-ring 38 fitted into groove 33. The two operating arms 12 when opened lie in a planar relation and stretch the sheath 34 in substantially a plane. Support tube 11 has a hollow retention nut 39 (FIG. 8) which is threaded on threaded end portion 22 and covers end portion 37 of sheath 34 to secure 0-ring 38 in groove 33. Support tube 11 has an enlarged portion 40 (FIG. 7) adjacent to pivot pins 28 which supports latex sheath 34 to retain its shape during opening of arms 12.

OPERATION

While the operation of this invention should be obvious from the foregoing description, it will be restated for clarity.

As noted above, laparoscopic retractor 10 is designed for manually maneuvering tissue which would otherwise obstruct the view from the operative site. The retractor 10 is an instrument which is sized for insertion through the laparoscope tube (not shown). Sheath 34 is installed on operating arms 12 with end portion 37 fitted over support tube enlarged portion 32 and 0-ring 38 fitted into groove 33. Retention nut 39 (FIG. 8) is threaded on threaded end portion 22 covering end portion 37 of sheath 34 to secure 0-ring 38 in groove 33. The instrument 10 is inserted, with the arms 12 closed, through the laparoscopic tube into the peritoneal cavity.

After the tissue or organ has been located by viewing the laparoscope, the arms 12 of the instrument 10 are opened by operation of the handle to spread the covering membrane 34. Arms 12, when opened, have a planar relation. Arms 12, when opened, have a planar relation. Rotation of knob 19 on threaded housing end portion 16 rotates actuator shaft 17 and threaded actuator screw 25 on threaded end portion 24 of actuator rod 13 and, since rod 13 is restrained from rotation, it is moved forward and backward in support tube 11. Forward movement of rod 13 operates links 29 to pivot arms 12 outward (FIGS. 3,4&9) to an opened position.

Figure 9:
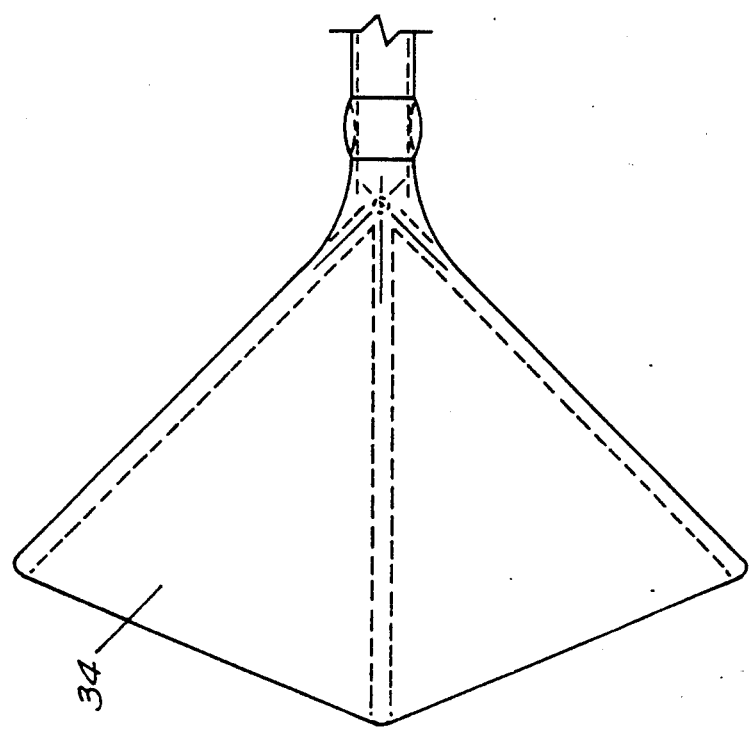
FIG. 9 is a front elevation of the operating end portion a laparoscopic retractor, as shown in FIG. 1, with the operating arms in an open position and the sheath of FIG. 5 stretched over the arms.

As seen in FIG. 9, the opening of operating arms 12 stretches sheath 34 to provide a membrane for manipulating tissue or organs in the peritoneal cavity. The arms 12 stretch sheath 34 in only one direction so that the stretched membrane is substantially planar. The maximum possible opened position is that shown in FIG. 3. Support tube enlarged portion 40 (FIG. 7) supports latex sheath 34 to retain its shape during opening of arms 12. The opened arms 12 and stretched planar membrane 34 inside the peritoneal cavity is then moved to displace the tissue or organ to allow the surgeon optimal viewing of the surgical field. On completion of use of the instrument 10, rotation of knob 19 in the opposite direction retracts rod 13 and links 29 pull operating arms 12 back inward to the position closed around rod 13 to permit removal of the instrument 10 through the laparoscopic tube. Of course, instrument 10 can be inserted through a surgical incision and operated as described, not necessarily through a laparoscopic tube.

While this invention has been shown fully and completely with special emphasis on certain preferred embodiments, it should be understood that within the scope of the appended claims the invention may be practiced otherwise than as specifically described herein.

I claim:

1. A laparoscopic retractor for manually maneuvering tissue which would otherwise obstruct the view from the operative site comprising
    an elongated, small-diameter body operable to be inserted through a small incision or through a laparoscopic tube into the peritoneal cavity,
    said body having exactly two operating arms pivotally supported on one end in a closed position for insertion into the peritoneal cavity and operable to support an expandable sheath, and
    means on the other end of said body operatively connected to said operating arms to move said arms to an opened position, in a substantially planar relation when inserted in the peritoneal cavity and to retract said arms to a closed position for removal therefrom,
    said body including means comprising an enlarged body portion with a peripheral groove adapted to receive the open end of a closed end tubular sheath when installed thereon for use and a retaining nut movable to secure said sheath in said groove,
    said two arms when moved to an opened position being operable to stretch a tubular sheath when installed thereon for manually maneuvering tissue which would otherwise obstruct the view from the operative site and when moved to a closed position being removable the operation site.

2. A laparoscopic retractor according to claim 1 in which
    said operatively connected means includes an actuating rod extendably and retractably movable in said body,
    means to extend and retract said rod, and
    means interconnecting said rod and said arms to pivot said two arms to an open position on extension of said rod and to a closed position on retraction of said rod.

3. A laparoscopic retractor according to claim 1 in which
    said operatively connected means includes an actuating rod extendably and retractably movable in said body,
    rotatable threaded means to extend and retract said rod,
    a knob for rotating said rotatable threaded means, and
    means for interconnecting said rod and said arms to pivot said two arms to an open position on extension of said rod and to a closed position on retraction of said rod.

4. A laparoscopic retractor according to claim 1 in which
    said operatively connected means includes an actuating rod extendably and retractably movable in said body,
    rotatable threaded means to extend and retract said rod,
    a knob for rotating said rotatable threaded means, and
    pivotal links interconnecting said rod and said two arms to pivot the same to an open position on extension of said rod and to a closed position on retraction of said rod.

5. A laparoscopic retractor assembly for manually maneuvering tissue which would otherwise obstruct the view from the operative site comprising
    an elongated, small-diameter body operable to be inserted through a small incision or through a laparoscopic tube into the peritoneal cavity,
    said body having exactly two operating arms pivotally supported on one end in a closed position for insertion into the peritoneal cavity and operable to support an expandable sheath,
    a sheath supported on said two operating arms comprising a tubular surgical latex closed at one end and having a diameter slightly larger than said body, and smaller than the laparoscopic tube or incision, and having an open end with an O-ring secured thereon,
    means on the other end of said body operatively connected to said two operating arms to move said arms to an opened position with said sheath extending therebetween, in a substantially planar relation, when inserted in the peritoneal cavity and to retract said two arms to a closed position for removal therefrom, and
    said body including means comprising an enlarged body portion with a groove receiving said O-ring on the open end of said closed end tubular sheath and a retaining nut tightened to secure said sheath in said groove while said arms are moved to an opened and to a closed position.

6. A laparoscopic retractor according to claim 5 in which
    said tubular surgical latex is about 14–15 mm in diameter at the smaller closed end and about 315 mm long.

7. A laparoscopic retractor according to claim 5 in which
    said operatively connected means includes an actuating rod extendably and retractably movable in said body,
    means to extend and retract said rod, and means interconnecting said rod and said two arms to pivot said arms to an open position on extension of said rod and to a closed position on retraction of said rod.

8. A laparoscopic retractor according to claim 5 in which
said operatively connected means includes an actuating rod extendably and retractably movable in said body,
rotatable threaded means to extend and retract said rod,
a knob for rotating said rotatable threaded means, and
means interconnecting said rod and said two arms to pivot said arms to an open position of said rod and to a closed position on retraction of said rod.

9. A laparaoscopic retractor according to claim 5 in which
said operatively connected means includes an actuating rod extendably and retractably movable in said body,
rotatable threaded means to extend and retract said rod,
a knob for rotating said rotatable threaded means, and
pivotal links interconnecting said rod and said two arms to pivot the same to an open position on extension of said rod and to a closed position on retraction of said rod.

* * * * *